United States Patent
Lallemand et al.

(10) Patent No.: US 9,107,822 B2
(45) Date of Patent: *Aug. 18, 2015

(54) WATER-IN OIL TYPE EMULSION FOR TREATING A DISEASE OF THE EYE

(75) Inventors: Frederic Lallemand, Fresnes (FR); Jean-Sebastien Garrigue, Verrieres-le-Buisson (FR); Betty Philips, Antony (FR)

(73) Assignee: SANTEN SAS, Evry (FR)

( * ) Notice: Subject to any disclaimer, the term of this patent is extended or adjusted under 35 U.S.C. 154(b) by 0 days.

This patent is subject to a terminal disclaimer.

(21) Appl. No.: 13/820,456

(22) PCT Filed: Sep. 2, 2011

(86) PCT No.: PCT/EP2011/065236
§ 371 (c)(1),
(2), (4) Date: Mar. 1, 2013

(87) PCT Pub. No.: WO2012/028733
PCT Pub. Date: Mar. 8, 2012

(65) Prior Publication Data
US 2013/0164285 A1    Jun. 27, 2013

Related U.S. Application Data

(63) Continuation-in-part of application No. 12/875,805, filed on Sep. 3, 2010.

(30) Foreign Application Priority Data

Sep. 3, 2010  (EP) .................................. 10175337

(51) Int. Cl.
| | |
|---|---|
| A61F 2/00 | (2006.01) |
| A61K 45/00 | (2006.01) |
| A61K 38/47 | (2006.01) |
| A61K 39/395 | (2006.01) |
| A61K 39/00 | (2006.01) |
| A61K 48/00 | (2006.01) |
| A61K 9/107 | (2006.01) |
| A61K 9/00 | (2006.01) |
| A61K 47/14 | (2006.01) |

(52) U.S. Cl.
CPC .............. *A61K 9/107* (2013.01); *A61K 9/0048* (2013.01); *A61K 9/0051* (2013.01); *A61K 47/14* (2013.01); *A61K 2039/505* (2013.01); *C07K 2317/24* (2013.01); *C07K 2317/55* (2013.01)

(58) Field of Classification Search
None
See application file for complete search history.

(56) References Cited

U.S. PATENT DOCUMENTS

| | | | |
|---|---|---|---|
| 2006/0121115 A1 | 6/2006 | Leroux et al. | 424/486 |
| 2008/0107694 A1* | 5/2008 | Trogden et al. | 424/400 |
| 2008/0268051 A1* | 10/2008 | Hughes et al. | 424/484 |
| 2012/0058187 A1 | 3/2012 | Lallemand et al. | 424/484 |

FOREIGN PATENT DOCUMENTS

| | | |
|---|---|---|
| CN | 1649567 A | 8/2005 |
| EP | 1 867 323 | 12/2007 |
| EP | 2 187 980 | 5/2010 |
| WO | WO 01/89479 | 11/2001 |
| WO | WO 01/93911 | 12/2001 |
| WO | WO 2009/039262 | 3/2009 |
| WO | WO 2009/046198 | 4/2009 |

OTHER PUBLICATIONS

Alany et al 2006. J. controlled release 111:145-152.*
Chan, et al. "Phase Transition Water-in-oil microemulsions as ocular drug delivery systems: In vitro and in vivo evaluation," International Journal of Pharmaceutics; 328 (1) pp. 65-71 (Jan. 2, 2007).
Tamilvanan, et al., "Oil-in-water lipid emulsions: implications for parenteral and ocular delivering systems," Progess in Lipid Research 43(6), pp. 489-533 (2004).
Kosvintsev S. R. et al. "Membrane emulsification: droplet size and uniformity in the absence of surface shear", Journal of Membrane Science, vol. 313, No. 1-2, Apr. 2008, pp. 182-189.

* cited by examiner

*Primary Examiner* — Christopher M Babic
*Assistant Examiner* — Kelaginamane T Hiriyanna
(74) *Attorney, Agent, or Firm* — Norton Rose Fulbright US LLP

(57) ABSTRACT

The invention relates to a composition for administering with a sustained release kinetic a therapeutically effective amount of a therapeutic agent to a subject in need thereof for treating diseases or conditions of the eye, wherein the composition is an water-in-oil type emulsion comprising an oil phase, a lipophilic surfactant dissolved in the oil phase, an aqueous phase dispersed in the oil phase, a hydrophilic therapeutic agent dissolved in the aqueous dispersed phase, and wherein the composition is intraocularly injectable, wherein the composition has a density lower than 1. The invention also relates to a pharmaceutical composition or to a medicament comprising the composition of the invention, and to a method for treating a condition or disease of the eye comprising administering a therapeutic amount of the composition of the invention. The invention also relates to a device comprising the composition of the invention.

15 Claims, 1 Drawing Sheet

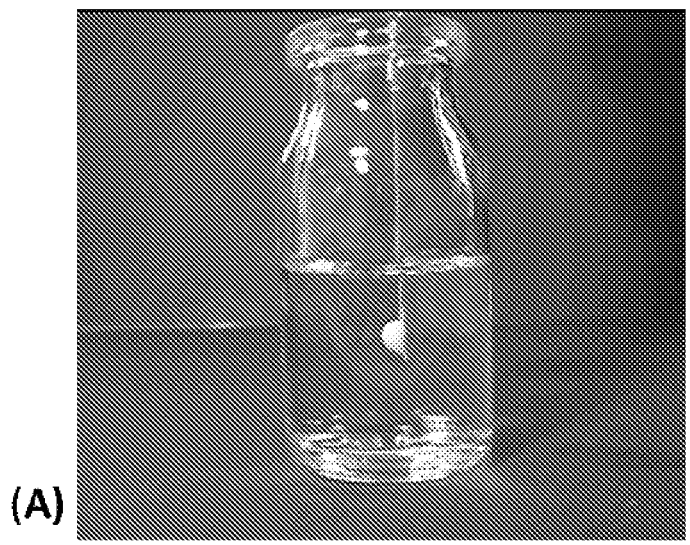
(A)
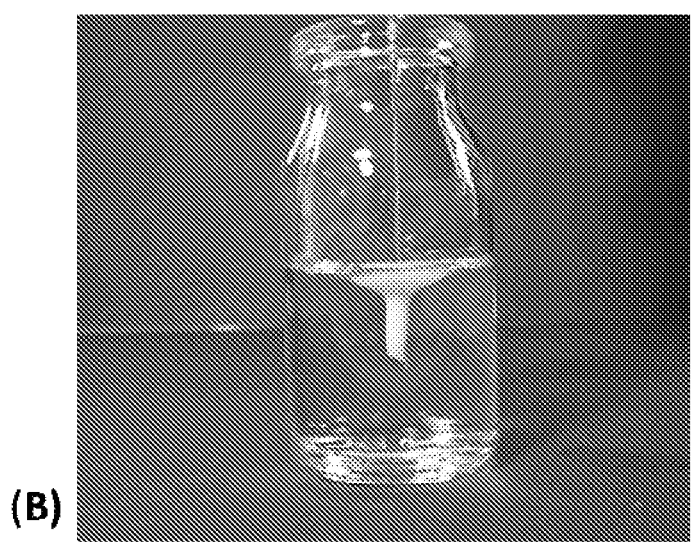
(B)
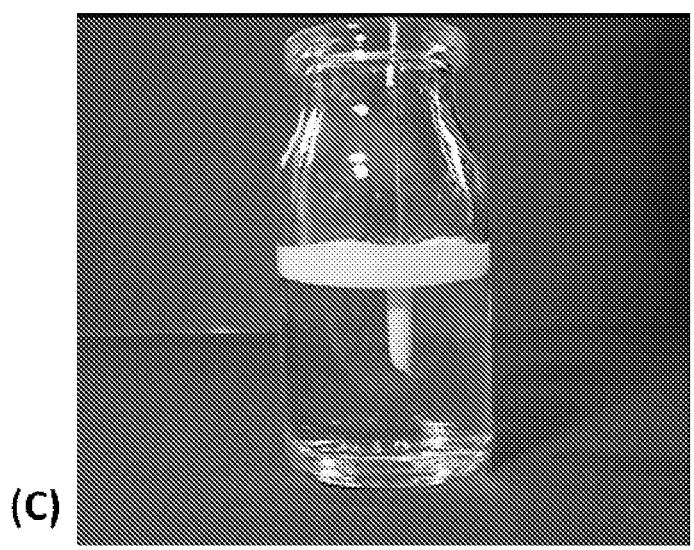
(C)

WATER-IN OIL TYPE EMULSION FOR TREATING A DISEASE OF THE EYE

CROSS-REFERENCE TO RELATED APPLICATIONS

This application is a national phase application under 35 U.S.C. §371 of International Application No. PCT/EP2011/065236 filed 2 Sep. 2011, which claims priority to U.S. patent application Ser. No. 12/875,805 filed 3 Sep. 2010, and European Patent Application No. 10175337.4 filed 3 Sep. 2010. The entire contents of each of the above-referenced disclosures is specifically incorporated herein by reference without disclaimer.

FIELD OF INVENTION

The present invention relates to the field of the treatment of the conditions or diseases of the eye through the intraocular administration of therapeutic agents.

BACKGROUND OF INVENTION

The treatment of eye diseases by injecting a therapeutic agent directly in the vitreous chamber has shown promising results in the past. Macugen® (oligonucleotide) and Lucentis® (monoclonal antibody) are pharmaceutical products which are efficient to treat retinal diseases.

However, their half-life in the vitreous is relatively short, leading to repeated injections to maintain the effect. The rapid clearance of these products is due to the renewal of the vitreous liquid over time.

This issue was already addressed in the prior art: for example, WO2009/046198 describes a method for administering a therapeutic agent in the vitreous with a sustained release kinetic; this method involves the formation of a macroscopic gel-like structure comprising said therapeutic agent, in the vitreous chamber. Also, EP2187980 describes the injection in the vitreous chamber of a therapeutic agent combined with a polymeric precursor, which will form in situ a hydrogel suitable for controlled release of said therapeutic agent.

However, the injection in the vitreous of a subject of a gel or gel-like structure as described in these patent applications may cause visual discomfort to the subject due to the invasion of the visual field by said gel or gel-like structure.

In further prior art documents, a solid implant may be injected in the eye of the subject for release of the active ingredient over several months. However, this form of administration introduces a solid body within the eye of the patient, which in some cases is not wished. Moreover, this approach is more adapted for administration of lipophilic agents than for administration of hydrophilic agents, and may not be selected for administration of biological agents such as proteins and monoclonal antibodies.

Therefore, there remains a need for a method for sustaineously releasing in the vitreous chamber, a composition comprising a hydrophilic therapeutic agent, such as for example a protein or a nucleic acid. Ensuring the visual comfort of the patient when the composition is within the vitreous body is another issue.

Surprisingly, the Applicant realized that a water-in-oil emulsion could be an efficient vehicle for administering hydrophilic therapeutic agents. Water-in-oil type emulsions are biphasic systems in which water droplets are dispersed within an oil phase.

The use of water-in-oil type emulsions as vehicles for sustained release of therapeutic agents is well known in the art. For example, WO01/89479 discloses the use of water-in-oil type emulsions for the parenteral administration of hydrophilic active ingredients with a sustained release kinetic.

This invention thus relates to the use of water-in-oil type emulsions for intraocular administration of a therapeutic agent to a subject in need thereof, providing a sustained release kinetic, and avoiding any invasion of the field of vision of the subject in his/her everyday life or safety issues.

An advantage of the solution proposed by the Applicant is that when injected intraocularly, the water-in-oil emulsion of the invention forms a reservoir of therapeutic agent that may be in the form of a layer or in the form of a bubble, having a lower density than the vitreous liquid. Therefore, when injected, the composition will rapidly (within 0.5 seconds to 1 minute) shift up from injection location to the upper part of the vitreous. Consequently, this liquid reservoir will float over the vitreous, out of the visual field, avoiding any visual discomfort for the subject to which the composition is administered. The therapeutic agent is then sustaineously released from the reservoir over a period of time ranging from two weeks to 6 months. The composition of the invention has the further advantage of being in physical contact with both vitreous body and targeted tissues such as, for example, the choroid or the retina, resulting in a targeted release of the therapeutic agent.

DEFINITIONS

In the present invention, the following terms have the following meanings:
- "Emulsion": colloidal system made of two non-miscible elements, for example oil and water. One element (the dispersed phase) is present on the form of droplets dispersed in the other element, constituting the continuous phase.
- "Water-in-oil type emulsion": emulsion made of water or aqueous droplets (i.e. the dispersed phase) dispersed in an oil phase (i.e. the continuous phase). A water-in-oil type emulsion also comprises surfactants (as defined hereafter), to avoid phase separation.
- "Sustained release kinetic": describes the slow release kinetic of a compound, at a predetermined rate and over an extended period of time.
- "Intraocular administration": injection of a product directly in the eyeball i.e. injection in the anterior chamber or in the posterior cavity (vitreous cavity) of the eye.
- "Surfactant": defines a substance that lowers the interfacial tension between two liquids.
- "Bioresorbable": defines a compound that progressively disappears in a biological environment.
- "Therapeutic agent": describes a molecule or a substance, preferably a biological molecule such as for example an oligonucleotide, a siRNA, a miRNA, a DNA fragment, an aptamer, a peptide, an antibody, a protein and the like, or a chemical entity, having the capacity, when administered in a suitable amount, of slowing down or stopping the progression, aggravation, or deterioration of one or more symptoms of a disease or condition; alleviates the symptoms of a disease or condition; cures a disease or condition.
- "Therapeutically effective amount": the amount of a therapeutic agent necessary and sufficient for slowing down or stopping the progression, aggravation, or deterioration of one or more symptoms of the disease or condition; alleviating the symptoms of the disease or condition; curing the disease or condition.

"Hydrophilic": defines a molecule or a portion of a molecule that is typically charge-polarized and capable of hydrogen bonding, enabling it to dissolve more readily in water than in oil or other solvents.

"Lipophilic": refers to a chemical compound capable to dissolve in fats, oils, lipids, and non-polar solvents.

"Non-miscible": liquid which does not combine or blend with another liquid, or which does not combine or blend immediately with another liquid.

"implant" is a solid dosage form which is implanted in a biological tissue usually composed of a polymer in which an active ingredient in incorporated to be slowly release.

"reservoir" is a reserve of active ingredient which can be solid of liquid.

SUMMARY

This invention relates to a composition for use in the treatment of a patient in need thereof by intraocular route, preferably by intraocular injection, of diseases or conditions of the eye, wherein the composition is a water-in-oil type emulsion comprising an oil phase, a lipophilic surfactant dissolved in the oil phase, an aqueous phase dispersed in the oil phase, a hydrophilic therapeutic agent dissolved in the aqueous dispersed phase, wherein the composition has a density lower than 1, preferably ranging from 0.91 to 0.97 g/cm$^3$. The density was measured by filling a calibrated volumetric flask with the emulsion and weighed on a balance. Volume/mass ratio is then calculated.

In a preferred embodiment, the viscosity of the composition ranges from 25 to 10 000 mPa·s at 20° C., as measured using a Kinexus Pro from Malvern U.K. at 20° C.

Preferably, the mean water droplet size ranges from 20 nm to 600 nm. In an embodiment, the mean water droplet size ranges from 25 nm to 500, preferably 30 to 200, more preferably 50-100 nm. In another embodiment, the mean water droplet size ranges from 20 nm to 100 nm. The mean particle size of the emulsions droplets was determined by quasi-elastic light scattering after dilution in water using a High Performance Particle Sizer (Malvern Instruments, UK).

The composition sustaineously releases the hydrophilic therapeutic agent within the eye.

In a preferred embodiment, the composition of the invention is for use in the treatment, by intraocular route, of diseases or conditions of the eye of a patient, wherein the composition is a water-in-oil type emulsion comprising an oil phase, a lipophilic surfactant dissolved in the oil phase, an aqueous phase dispersed in the oil phase, a hydrophilic therapeutic agent dissolved in the aqueous dispersed phase, and wherein the composition has a density lower than 1, preferably ranging from 0.91 to 0.97 g/cm$^3$, and wherein the composition has a viscosity ranging from 25 to 10 000 mPa·s at 20° C., and wherein the size of the droplets of water ranges from 20 nm to 600 nm, and wherein the use by intraocular route is intraocular injection.

According to an embodiment, the oil phase is selected from the group comprising triglycerides such as, for example, medium chain or long chain triglycerides, monoglycerides, diglycerides, vegetable oils or mineral oils.

Preferably, the lipophilic surfactant is selected from the group comprising sorbitan ester such as, for example, sorbitan stearate, sorbitan laurate and sorbitan monopalmitate; bentonite; glycerol monostearate; propylene glycol monolaurate and mixtures thereof.

In a preferred embodiment, the aqueous phase is present in the composition of the invention in an amount ranging from 0.1 to 70% in weight to the total weight of the composition, preferably from 2 to 50% w/w, more preferably from 10 to 30% w/w.

Preferably, the hydrophilic therapeutic agent is selected from the group comprising monoclonal antibodies (full or Fab fragment), such as for example ranibizumab, bevacizumab, trastuzumab, cituximab or rituximab;

anti-angiogenic molecules, such as for example pegaptanib;

ROCK (Rho-kinases) inhibitors, such as for example fasudil;

proteins such as anti-CD160 S-HLA-G or WNT3A protein which activates WNT (Wingless—Integration site) for survival of photoreceptor cells;

growth factors such as epithelium growth factors (EGF), anti-EGF or TGF (Transforming growth factor);

siRNA such as siRNA anti-arginase;

miRNA;

oligonucleotides such as antisens DNA or antisens RNA;

iron chelating molecules such as deferiprone and salicylaldehyde isonicotinoyl hydrazone;

anti-inflammatory molecules such as epigallocatechin gallate;

antibiotics for back of the eye infection such as linezolide, clavulamic acid, macrolides;

anti-inflammatory molecules preferably selected from the group comprising corticosteroids such as dexamethasone and its hydrophilic derivatives; and mixtures thereof.

In one embodiment of the invention, the composition further comprises a lipophilic therapeutic agent in the oil phase, said lipophilic therapeutic agent being selected from the group comprising cyclosporine A, lutein, alpha-tocopherol and dexamethasone palmitate.

According to the invention, the composition may further comprise viscosity modifying agents, such as, for example an hydrogel of sodium hyaluronate, carbopol gels, hydroxyethyl cellulose, dextran, carboxymethyl cellulose, polyethylene glycol, polyvinyl alcohol, collagen, and/or pH buffering agents, such as, for example, phosphate, citrate, tris, histidine or acetate buffer, and/or osmolality modifying agents, such as, for example NaCl, KCl, CaCl$_2$, glycerol, mannitol, alpha-trehalose or propylene glycol.

In a preferred embodiment, the composition of the invention is intravitreally injectable.

The diseases or conditions of the eye that may be treated with the composition of the invention are preferably selected from the group comprising glaucoma, anterior uveitis, retinal oxidation, age related macular degeneration, posterior uveitis, diabetic macular edema and central vein occlusion.

This invention also relates to a pharmaceutical composition comprising the composition of the invention, and further comprising one or more pharmaceutically acceptable excipients.

This invention also relates to a medicament comprising a water-in-oil type emulsion as described above.

This invention also relates to a method for treating a condition or disease of the eye, which comprises administering to a patient in need thereof by intraocular route, a composition of the invention, wherein a therapeutic amount of a hydrophilic therapeutic agent is dissolved in the aqueous dispersed phase. In the method of the invention, said therapeutic agent is sustaineously released within the eye of the patient.

In an embodiment, the volume of the injected composition ranges from 5 to 250 microliters.

In an embodiment, the composition or the medicament is injected in the vitreous chamber or in the anterior chamber of the eye of the patient.

This invention also relates to a device comprising the composition or the medicament according to the invention. According to an embodiment, the device comprises a volume of 20 to 350 microliters of the composition of the invention.

According to a preferred embodiment, the composition, the pharmaceutical composition, the medicament or the device are not implants.

DETAILED DESCRIPTION

The invention thus relates to a composition for use in the treatment by intraocular route of diseases or conditions of the eye, wherein the composition is a water-in-oil type emulsion comprising an oil phase, a lipophilic surfactant dissolved in the oil phase, an aqueous phase dispersed in the oil phase and a hydrophilic therapeutic agent dissolved in the aqueous dispersed phase, the composition having a density lower than 1, a viscosity ranging from 25 to 10000 mPa·s at 20° C., wherein the mean size of the droplets of water ranges from 20 nm to 600 nm, said composition sustaineously releasing the hydrophilic therapeutic agent, and wherein the use by intraocular route is intraocular injection.

In one embodiment of the invention, the oil phase of the water-in-oil type emulsion comprises an oil selected from the group comprising triglycerides such as, for example semi-synthetic oils: medium chain triglycerides (MCT) or long chain triglycerides; monoglycerides, diglycerides or vegetable oils such as, for example, castor oil or mineral oils. According to a particular embodiment of the invention, the emulsion is deprived of ethyl oleate, soybean oil or mixture thereof.

In a particular embodiment of the invention, the amount of oil phase in the water-in-oil type emulsion ranges from 30 to 99.9% in weight to the weight of the total emulsion, preferably from 50 to 98% w/w, more preferably from 70 to 90% w/w.

In one embodiment of the invention, the emulsion comprises one or more lipophilic surfactants, in an amount sufficient for ensuring the water-in-oil type of the emulsion. In a particular embodiment of the invention, said lipophilic surfactants are selected from the group comprising sorbitan ester such as, for example, sorbitan stearate and sorbitan monopalmitate, bentonite, glycerin monostearate, glyceryl monooleate and propylene glycol monolaurate or mixtures thereof, poloxamer 188, poloxamer 282, poloxamer 407, tyloxapol, vitamin E D-polyethylene glycol succinate, cetostearyl alcohol, cholesterol, ethylene glycol palmitostearate, lauric acid, myristic acid, myristyl alcohol, linoleic acid, oleic acid, palmitic acid, stearic acid oleyl alcohol. According to one embodiment, the emulsion is deprived of at least one surfactant selected from the group consisting of sorbitan mono laurate, polyoxyethylene sorbitan mono oleate, polysorbate 20 (Tween 20), sorbitan trioleate (Span 85), phospholipids such as egg lecithin or mixture thereof.

In a particular embodiment of the invention, the HLB (hydrophilic—lipophilic Balance) of the surfactants of the composition ranges from 0 to 9, preferably from 2 to 8.

In a particular embodiment of the invention, the amount of lipophilic surfactants in the water-in-oil type emulsion ranges from 0.1 to 10% in weight to the weight of the total emulsion, preferably from 0.5 to 5% w/w, more preferably from 1 to 2% w/w.

In one embodiment of the invention, the aqueous phase in the water-in-oil type emulsion is present in an amount ranging from 0.1 to less than 50% in weight to the weight of the total emulsion, preferably from 0.5 to 15% w/w, more preferably from 2 to 10% w/w. Preferably, said aqueous phase is water or is essentially composed of water.

In a particular embodiment of the invention, the composition includes one or more hydrophilic therapeutic agent(s) present in the aqueous droplets of the water-in-oil type emulsion.

In one embodiment of the invention, the hydrophilic therapeutic agent is selected from the group comprising monoclonal antibodies (full or fragment Fab), such as for example ranibizumab, bevacizumab trastuzumab, cituximab and rituximab; anti-angiogenic molecules, such as for example pegaptanib; a ROCK (Rho-kinases) inhibitor, such as for example fasudil; proteins such as anti-CD160 S-HLA-G; WNT3A protein which activates WNT (Wingless—Integration site) for survival of photoreceptor cells; growth factors such as epithelium growth factors (EGF), anti-EGF or TGF (Transforming growth factor); siRNA such as siRNA anti-arginase, miRNA; oligonucleotides such as antisens DNA or antisens RNA; iron chelating molecules such as deferiprone and salicylaldehyde isonicotinoyl hydrazone; anti-inflammatory molecules such as epigallocatechin gallate; or antibiotics for back of the eye infection such as linezolide, clavulamic acid, macrolides, anti-inflammatory molecules preferably selected from the group comprising cortico-steroids such as dexamethasone and its hydrophilic derivatives and mixtures thereof.

In an embodiment of the invention, the amount of hydrophilic therapeutic ingredient in the emulsion ranges from 0.01 to 10% in weight to the total weight of the emulsion, preferably from 0.05 to 5% w/w, more preferably from 0.1 to 1% w/w.

In a particular embodiment of the present invention, the hydrophilic therapeutic agent is not a drug complex comprising a therapeutic agent and a polymer.

In an embodiment of the invention, the emulsion further comprises one or more lipophilic therapeutic agents in the oil phase. In a preferred embodiment of the invention, said lipophilic therapeutic agent is selected from the group comprising cyclosporine A, lutein, alpha-tocopherol and dexamethasone palmitate.

In a preferred embodiment, the amount of lipophilic therapeutic ingredient in the emulsion ranges from 0.01 to 10% in weight to the total weight of the emulsion, preferably from 0.05 to 5% w/w, more preferably from 1 to 2% w/w.

In a particular embodiment of the present invention, the lipophilic therapeutic agent is not a drug complex comprising a therapeutic agent and a polymer.

In a particular embodiment of the present invention, the water-in-oil emulsion is deprived of at least one metabolic degradation enzyme inhibitors selected from the group consisting of CYP3A inhibitors, protease inhibitors like aprotinin, chymostatin, bacitracin, benzamidine, phosphoramidon, leupeptin, bestatin, cystatin, amastatin, pepstatin, potato carboxypeptidase, soybean trypsin inhibitor, diisopropylfluorophosphate or EDTA. In another particular embodiment of the present invention, the water-in-oil emulsion is deprived of at least one drug-efflux P-glycoprotein enzyme inhibitors selected from the group consisting of flavonoids contained in fruit juices such as naringenin, isoquercetin, quercetin or vitamin E tocopheryl glycolsuccinate (TPGS).

The water-in-oil type emulsion of the invention presents a lower density than the vitreous liquid which has a density equivalent, if not equal, to the density of water. According to the invention, the density of the water-in-oil type emulsion of the invention is less than 1. Preferably, the density of the water-in-oil type emulsion ranges from 0.90 to 0.99, preferably from 0.91 to 0.97, more preferably from 0.93 to 0.96. Therefore, when injected in the vitreous body, the emulsion will be located over the vitreous liquid.

Also, when injected, the composition will form a non-breakable reservoir. According to one embodiment, the reservoir has the form of a bubble. The fact that the bubble does not break into several drops is linked to the surface tension, to the interfacial tension and to the viscosity of the composition. These three physico-chemical properties of the composition may be considered as close to the one of the oil phase used in the composition. As a matter of example, medium chain triglycerids (MCT) present a surface tension of 30 mN/m, an interfacial tension of 45 mN/m and viscosity ranging from 27 to 33 mPa·s at 20° C. and this combination of physico-chemical properties avoids MCT to break into several oil drops.

According to one embodiment, the viscosity of the composition is ranging from 5 to 10 000 mPa·s at 20° C. depending on the amount of water emulsified in the oil, preferably ranging from 25 to 5000 mPa·s at 20° C., preferably ranging from 24 to 1000 mPa·s at 20° C., preferably ranging from 25 to 500 mPa·s at 20° C. According to one embodiment, the viscosity of the composition is ranging from 5 to 100 mPa·s at 20° C., preferably from 5 to 50 mPa·s at 20° C., more preferably from 5 to 20 mPa·s at 20° C. According to another embodiment, the viscosity of the composition is ranging from 100 to 10 000 mPa·s at 20° C., preferably from 500 to 10 000 mPa·s at 20° C., more preferably from 5000 to 10 000 mPa·s at 20° C. According to the invention, the viscosity is measured using a Kinexus Pro from Malvern U.K. at 20° C.

According to one embodiment, the surface tension of the composition is ranging from 0 to 30 mN/m, preferably ranging from 5 to 20 mN/m, more preferably ranging from 10 to 15 mN/m.

According to one embodiment, the interfacial tension of the composition is ranging from 0 to 45 mN/m, preferably ranging from 5 to 30 mN/m, more preferably ranging from 10 to 20 mN/m.

The water-in-oil type emulsion of the invention is efficient for sustained release administration of a therapeutic agent. According to one embodiment, the therapeutic agent is released for a period of time ranging from 2 weeks to 12 months, preferably from 1 month to 6 months.

The sustained release effect is provided by the migration of water droplets dispersed in the continuous oil phase to the surface of the oil reservoir formed by the emulsion when injected in the eye. In one embodiment of the invention, the sustained release kinetic can be adapted to the exact need of the patient.

In a first embodiment of the invention, said sustained release kinetic may depend on the viscosity of the oil phase. Indeed, the more viscous the oil phase is, the more extended the period of release may be, as evidenced by the Stokes law:

$$v_s = \frac{2}{9}\frac{(\rho_p - \rho_f)}{\mu}gR^2$$

where:
- $v_s$ is the particles' settling velocity (m/s) (vertically downwards if $\rho p > \rho f$, upwards if $\rho p < \rho f$),
- g is the gravitational acceleration (m/s$^2$),
- $\rho p$ is the mass density of the particles (kg/m$^3$), and
- $\rho f$ is the mass density of the continuous phase (kg/m3).
- R the radius of the particle.
- µ is the viscosity of the continuous phase The Stokes law states that the speed of movement of a particle (water droplet), in a continuous phase (oil phase), is inversely proportional to the viscosity (µ) of the continuous phase. Therefore, the higher the viscosity of the oil phase of the emulsion is, the slower the water droplets will move to the surface of the oil reservoir to release the therapeutic agent. With viscous oil such as long chain triglycerides, the release of the therapeutic agent may be extended up to one year. According to an embodiment, the viscosity of the oil phase ranges from 1 to 10000 mPa·s at 20° C., preferably from 10 to 5000 mPa·s at 20° C., even more preferably from 25 to 1000 mPa·s at 20° C.

In a second embodiment of the invention, said sustained release kinetic may depend on the size of the water droplets dispersed in the oil phase. Indeed, a bigger water droplet will move faster than a smaller as described by the Stokes law. Therefore, the smaller the droplets are, the longer their migration to the surface of the injected reservoir may be, and then the more extended the period of release of the therapeutic agent may be. For example, for comparable compositions of the invention in terms of ingredients, an emulsion with a droplet size of more than 1 µm may release the therapeutic agent in about 1 week to 2 months, whereas the release may be increased to more than 2 months when the droplet size is below 500 nm. According to an embodiment, the size of the water droplets in the emulsion of the invention ranges from 1 to 2000 nm, preferably from 10 to 1000 nm, more preferably from 20 to 600 nm.

In a third embodiment of the invention, said sustained release kinetic may be conditioned by the volume of the injected water-in-oil type emulsion. The bigger the emulsion reservoir is, the more extended the period of release may be. Indeed, the bigger the emulsion reservoir is, the longer the road of the water droplet to reach the surface of the reservoir is. Preferably, a volume of the composition of the invention ranging from 5 to 250 µL, preferably from 10 to 100 µL, more preferably about 50 µL is injected.

In a fourth embodiment of the invention, the viscosity of the aqueous phase is increased in order to enhance the sustained release. In a particular embodiment of the invention, said viscosity is increased by addition of a viscosity modifying agent selected from the group comprising sodium hyaluronate, carbopol gels, hydroxyethyl cellulose, dextran, carboxymethyl cellulose, PEG, polyvinyl alcohol, collagen. In a preferred embodiment of the invention, said hydrogel is made of cellulose, hyaluronic acid, and/or collagen.

In a particular embodiment of the present invention, the water-in-oil emulsion is deprived of organogelling agent such as amino acid derivatives, especially fatty acid ester derivatives of amino acids, more specifically alanine ester derivatives. In this particular embodiment, organogelling agents refer to molecules which have the capacity to self-assemble spontaneously via bonds of low energy to form a matrix that immobilizes hydrophobic organic liquid. In a particular embodiment, the water-in-oil emulsion of the present invention is not a phase transition system.

In a fifth embodiment of the invention, the means for sustaineously releasing the therapeutic agents as described in the first to four embodiments hereabove, may be combined one to each other or all together in order to modulate the sustain release effect.

According to an embodiment of the invention, the aqueous phase of the emulsion further comprises a pH modifying agent or a pH buffering agent. In a preferred embodiment, said pH buffering agent is selected from the group comprising phosphate, citrate, tris, histidine or acetate buffers. In a preferred embodiment, said pH buffering agent is a phosphate buffer. In one embodiment of the invention, the amount of said agent for modifying the pH of the aqueous phase ranges from 0.05 to 10% in weight to the total weight of the aqueous phase, preferably from 0.01 to 5% w/w, more preferably from 0.1 to 1% w/w.

According to an embodiment of the invention, the aqueous phase of the emulsion further comprises an agent for modifying the osmolality of the aqueous phase of the emulsion. In a first embodiment, said agent for modifying the osmolality is selected from the group comprising NaCl, KCl and $CaCl_2$. In a second embodiment, the modification of the osmolality of the composition results from the addition of a compound selected from the group comprising neutral compounds such as, but not limited to, glycerol, mannitol, alpha-trehalose or propylene glycol. In a preferred embodiment, the modification of the osmolality of the composition results from the addition of 0.5-2%, preferably 0.9% w/w of NaCl, 0.5-10%, preferably 3-5% w/w of alpha-trehalose or mannitol or propylene glycol in weight to the weight of the total emulsion.

In a particular embodiment, water-in-oil emulsions of the present invention are not double emulsions (i.e. water-in-oil-in-water or oil-in-water-in-oil emulsions).

According to an embodiment, the composition is intraocularly injectable. Preferably, the composition is intravitreally injectable.

The water-in-oil type emulsion according to the invention is bioresorbable. In one embodiment of the invention, the oily reservoir is resorbed in a period of time ranging from 1 to 24 months after injection, preferably from 6 to 18 months after injection, more preferably about 12 months after injection.

The water-in-oil type emulsion according to the invention is for treating diseases or conditions of the eye. In one embodiment of the invention, said diseases or conditions of the eye are selected from the group comprising glaucoma, anterior uveitis retinal oxidation, age related macular degeneration, posterior uveitis, diabetic macular edema and central vein occlusion.

The present invention also relates to a pharmaceutical composition according to the water-in-oil type emulsion of the invention. In one embodiment of the invention, the pharmaceutical composition further comprises at least one pharmaceutically acceptable excipient.

The present invention also relates to a medicament according to the water-in-oil type emulsion of the invention.

The present invention also relates to a device for administering the water-in-oil type emulsion, the pharmaceutical composition or the medicament according to the invention. Preferably, said device is a prefilled syringe comprising 20 μL to 350 μL of the composition of the invention. In one embodiment of the invention, said device contains the pharmaceutical composition or the medicament according to the invention.

Also, the present invention relates to a method for treating a condition or disease of the eye, comprising administering intraocularly a therapeutic amount of the composition or of the medicament of the invention. Preferably, the method of the invention comprises the injection, preferably in the vitreous chamber, of a volume ranging from 5 to 250 μL preferably from 10 to 100 μL, more preferably of about 50 μL. In a preferred embodiment, said composition or medicament is injected less than once a week, preferably less than once a month, more preferably less than once in six months. According to an embodiment, the injected composition forms in situ a reservoir within which the aqueous phase migrates towards the surface of the reservoir, letting the therapeutic agent be sustaineously released to the vitreous chamber or the targeted tissue. According to one embodiment, the reservoir has the form of a bubble. According to another embodiment, the reservoir has the form of a spread bubble. According to another embodiment, the reservoir has the form of a layer, floating over the vitreous liquid.

The water-in-oil emulsion of the invention may be manufactured either through a conventional process or through a process called membrane emulsification.

In the conventional process, the oily phase components are successively weighed in the same beaker and then magnetically stirred under a slight heating (30-50° C., preferably 40° C.) until a slightly viscous phase is obtained. Aqueous phase components are successively weighed in the same beaker and then magnetically stirred under a slight heating (30-50° C., preferably 40° C.) until a transparent, limpid and fluid phase is obtained. Both phases are heated (to 50-80° C., preferably 65° C.). The emulsion droplet size may be decreased by high sheer mixing a 5 minutes high shear mixing with a POLYTRON PT 6100. The emulsion may be homogenized in a microfluidizer (C5, Avestin).

An alternative manufacturing process is membrane emulsification: the emulsions of the invention may also be manufactured by membrane emulsification as described by Serguei (Serguei R. Kosvintsev, Gilda Gasparini, Richard G. Holdich, Membrane emulsification: droplet size and uniformity in the absence of surface shear, Journal of Membrane Science, Volume 313, Issues 1-2, 10 Apr. 2008, Pages 182-189). In this alternative process, the oily phase components are successively weighed in the same beaker and then magnetically stirred under a slight heating (30-50° C., preferably 40° C.) until a slightly viscous phase is obtained. Aqueous phase components are successively weighed in the same beaker and then magnetically stirred under a slight heating (30-50° C., preferably 40° C.) until a transparent, limpid and fluid phase is obtained. Both phases are heated (to 50-80° C., preferably 65° C.). Aqueous phase is forced through a membrane with 1 μm pores. The water droplets are collected by a continuous flux of the oily phase.

BRIEF DESCRIPTION OF THE DRAWINGS

FIG. 1 represents photographs showing the injection of 60 μL of the composition of example 1 in a glass of water and behavior of the composition 16 seconds (FIG. 1A), 24 seconds (FIG. 1B) and 1 minute (FIG. 1C) after injection.

EXAMPLES

The present invention is further illustrated by the following examples.

Example 1

Composition

This composition is a water-in-oil emulsion as described in the specification, obtained by either one of the manufacturing processes described below using the following ingredients in indicated amounts:

| Ingredients | Concentration % w/w |
|---|---|
| Ranibizumab | 0.1% |
| Water for injection | 4% |
| Dihydrated alpha, alpha-trehalose | 3% |

-continued

| Ingredients | Concentration % w/w |
|---|---|
| Monohydrated histidine chlorhydrate histidine | 0.05% |
| Sorbitan stearate | 2% |
| Medium chain triglyceride | Qs 100% |

Manufacturing Process:

The oily phase components were successively weighed in the same beaker and then magnetically stirred under a slight heating until a slightly viscous phase is obtained. Aqueous phase components were successively weighed in the same beaker and then magnetically stirred under a slight heating (40° C.) until a transparent, limpid and fluid phase is obtained. Both phases were heated to 65° C. The coarse emulsion is formed by rapid addition of the aqueous phase in the oily phase. The emulsion is white and slightly transparent. The emulsion droplet size is decreased by applying a 5 minute high shear mixing with a POLYTRON PT 6100. The emulsion became milky. The emulsion temperature was cooled down to 20° C.

The final emulsion was obtained by homogenization in a microfluidizer (C5, Avestin) using continuous cycles for 5 min at a pressure of 10 000 psi. The emulsion was milky and very fluid. The emulsion temperature was decreased to 25° C.

Characterization:

Emulsion was conditioned in glass vials with nitrogen bubbling and then sterilized in an autoclave 20 minutes at 121° C. The mean particle size of the emulsions droplets was determined by quasi-elastic light scattering after dilution in water using a High Performance Particle Sizer (Malvern Instruments, UK). The electrophoretic mobility was measured at 25° C. in a Malvern Zetasizer 2000 (Malvern Instruments, UK) following a 1:200 dilution in double distilled water as detailed above and converted into zeta potential through the Smoluchowski equation. The viscosity is measured using a Kinexus Pro from Malvern U.K. at 20° C. The density was measured by filling a calibrated volumetric flask with the emulsion and weighed on a balance. Volume/mass ratio is then calculated.

Specifications of the Composition of Example 1:

| Size of the water droplets | Density | In vitro release time of ranibizumab |
|---|---|---|
| 500 nm | 0.94 g/cm³ | 2 months |

In vitro release test is performed by incubating at 37° C., 20 μL of the composition in 4 mL of water. Quantification of active ingredient release in water is done by HPLC. At 2 months the entire quantity of ranibizumab was released in the water.

An in vitro test of injection was performed by injecting 60 μL of composition of example 1 in water. As shown in FIG. 1, the composition reaches the surface as soon as injected in the aqueous media. This result is linked to the density of the composition that is lower than water's.

Example 2

Composition Comprising Sodium Pegaptanib

| Ingredients | Concentration |
|---|---|
| Sodium pegaptanib | 0.8% |
| Water for injection | 5% |
| Glycerol monostearate | 0.5% |
| Sorbitan monopalmitate | 1% |
| Medium chain triglyceride | Qs 100% |
| Dexamethasone palmitate | 1.2% |

Specifications of the Composition of Example 2:

| Size of the water droplets | Density | In vitro release time of pegaptanib |
|---|---|---|
| 200 nm | 0.95 g/cm³ | 4 months |

As in example 1, in vitro release test is performed by incubating at 37° C. 20 μL of the composition in 4 ml of water. Quantification is done by HPLC.

Compared to example 1, and in accordance with the Stokes law, with a decrease of the water droplet size the release time has doubled, confirming that size of the dispersed droplets is a key factor in the release rate of the hydrophilic active ingredient.

The invention claimed is:

1. A composition comprising a water-in-oil emulsion comprising an oil phase, a lipophilic surfactant dissolved in the oil phase, an aqueous phase dispersed in the oil phase, a hydrophilic therapeutic agent dissolved in the aqueous dispersed phase, and wherein the composition:
   has a density lower than the density of water;
   has a viscosity ranging from 25 to 10 000 mPa·s at 20° C.;
   has droplets of water ranging from 20 nm to 600 nm; and
   is formulated for intraocular injection.

2. The composition of claim 1, wherein the composition has a density ranging from 0.91 to 0.97 g/cm³.

3. The composition of claim 1, wherein the oil phase comprises at least one triglyceride, monoglyceride, diglyceride, vegetable oil, or mineral oil.

4. The composition of claim 3, further defined as comprising a medium chain or long chain triglyceride.

5. The composition of claim 1, wherein the lipophilic surfactant comprises at least one sorbitan ester, bentonite, glycerol monostearate, or propylene glycol monolaurate.

6. The composition of claim 5, further defined as comprising sorbitan stearate, sorbitan laurate, or sorbitan monopalmitate.

7. The composition of claim 1, wherein the aqueous phase is present in an amount ranging from 0.1 to less than 50% in weight to the total weight of the composition.

8. The composition of claim 7, wherein the aqueous phase is present in an amount ranging from 0.5 to 15% w/w.

9. The composition of claim 8, wherein the aqueous phase is present in an amount ranging from 2 to 10% w/w.

10. The composition of claim 1, wherein the hydrophilic therapeutic agent is a monoclonal antibody (full or fragment Fab), an anti-angiogenic molecule, a ROCK (Rho-kinases) inhibitor, a protein, WNT3A protein, a growth factor, a siRNA, an oligonucleotide, an iron chelating molecule, an anti-inflammatory molecule, an antibiotic, or a cortico-steroid.

11. The composition of claim 10, wherein the hydrophilic therapeutic agent is ranibizumab, bevacizumab trastuzumab, cituximab, rituximab, pegaptanib, fasudil, anti-CD160 S-HLA-G, epithelium growth factors (EGF), anti-EGF, TGF (Transforming growth factor), siRNA anti-arginase, miRNA, antisense DNA, antisense RNA, deferiprone, salicylaldehyde isonicotinoyl hydrazone, epigallocatechin gallate, linezolide, clavulamic acid, macrolide, or dexamethasone including its hydrophilic derivatives.

12. The composition of claim 1, further comprising a lipophilic therapeutic agent dissolved in the oil phase, the lipophilic therapeutic agent further defined as comprising cyclosporine A lutein, alpha-tocopherol, and/or dexamethasone palmitate.

13. The composition of claim 1, further comprising viscosity modifying agents, pH buffering agents, and/or osmolality modifying agents.

14. The composition of claim 13, further defined as comprising at least one of a hydrogel of sodium hyaluronate, carbopol gel, hydroxyethyl cellulose, dextran, carboxymethyl cellulose, PEG, polyvinyl alcohol, collagen; phosphate, citrate, tris, histidine, or acetate buffer; NaCl, KCl, $CaCl_2$, glycerol, mannitol, alpha-trehalose and/or propylene glycol.

15. The composition of claim 1, further comprising one or more pharmaceutically acceptable excipient.

* * * * *

UNITED STATES PATENT AND TRADEMARK OFFICE
CERTIFICATE OF CORRECTION

PATENT NO. : 9,107,822 B2  
APPLICATION NO. : 13/820456  
DATED : August 18, 2015  
INVENTOR(S) : Frederic Lalleman et al.

It is certified that error appears in the above-identified patent and that said Letters Patent is hereby corrected as shown below:

On the Title page, Item (54), and in the Specification, column 1, line 1, please delete "WATER-IN OIL" and replace with --WATER-IN-OIL-- therefor.

Signed and Sealed this  
Twenty-third Day of February, 2016

Michelle K. Lee  
*Director of the United States Patent and Trademark Office*